US005924292A

United States Patent [19]
Markum

[11] Patent Number: 5,924,292
[45] Date of Patent: Jul. 20, 1999

[54] DEODORIZING ELEMENT FOR ELIMINATING REFRIGERATOR ODORS

[75] Inventor: Randall Markum, Lamar, Ala.

[73] Assignee: Emerson Electric Company, St. Louis, Mo.

[21] Appl. No.: 09/008,766

[22] Filed: Jan. 19, 1998

[51] Int. Cl.[6] .................................................. F24F 3/16
[52] U.S. Cl. ............................................. 62/78; 422/122
[58] Field of Search ................................. 62/78; 422/122

[56] References Cited

U.S. PATENT DOCUMENTS

| | | | |
|---|---|---|---|
| 4,948,567 | 8/1990 | Atarashiya | 62/78 |
| 4,955,208 | 9/1990 | Kawashima et al. | 62/78 |
| 5,291,742 | 3/1994 | Kawatani et al. | 62/78 |
| 5,347,820 | 9/1994 | In Gweon | 62/78 |

Primary Examiner—Ronald Capossela
Attorney, Agent, or Firm—Polster, Lieder, Woodruff & Lucchesi

[57] ABSTRACT

A deodorizing element (10) for use in a refrigerator (1). The element acts to remove food odors from the air circulating through the refrigerator which has a refrigeration system (5) by which air is circulated throughout a food storage compartment (2–4). The deodorizing element comprises a metal rod (14) at each end of which are electrical connections (16a, 16b) for connecting the heating element into an electrical circuit by which current is drawn through the rod. A layer (24) of a coating material is formed on the outer surface of the rod. This coating material is an odor absorbing material which is activated by the heat generated when current flows through the heating rod. The heating rod is mounted in an air circulation path of the refrigeration system by which air flowing through the system is drawn over the heating element and odors in the air are absorbed by the coating material.

14 Claims, 2 Drawing Sheets

DEODORIZING ELEMENT FOR ELIMINATING REFRIGERATOR ODORS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to refrigerators in which food is stored, and more particularly, to a coated heating element installed in a refrigerator which reduces or eliminates food odors which may otherwise permeate throughout the food storage compartment of the refrigerator.

Refrigerators such as commonly found in households are used to store a wide variety of foods. Many of these foods give off distinctive odors. It is both unappealing and unappetizing to retrieve food from the refrigerator which is permeated with the odor of some other food. Wrapping food in a sealed container, a plastic bag, foil wrapping, etc., is one way foods which are particularly odorous can be prevented from contaminating other foods with their smell. However, this does not always work. The food may be improperly wrapped, or the bag or foil inadvertently opened during handling, being moved about within the refrigerator, or when other food is placed on top of, or beside, the package thereby displacing part of the wrapper.

In addition to wrapping the food, refrigerators have compartments in which foods can be stored so as to minimize any odors they give off. It is also known that putting baking soda or other odor absorbing powders in the refrigerator can reduce the effect of one food's odor on another. Another approach has been to install a deodorizing element in the refrigerator as part of the refrigerator's air cooling system. As shown, for example, in U.S. Pat. Nos. 5,347,820, 5,291,742, 5,290,510, and 4,948,567, deodorizing elements of various constructions have been utilized to perform this deodorizing function. The deodorizing element is installed in the air circulation portion of the refrigerator by which cold or cooled air is directed through the freezer and refrigerated portions of the appliance. The deodorizing element is, for example, a glass tube whose outer surface is coated with an adsorbent material which is activated when electricity is supplied to the heating element so to remove any food odors in the circulating air. While this approach is effective, there is a cheaper, more efficient, less costly way of achieving this same result.

BRIEF SUMMARY OF THE INVENTION

Among the several objects of the present invention may be noted the provision of a heating element for installation in a refrigerator in which food is stored;

the provision of such a heating element to be a coated heating element which, when an electrical current is supplied to the element, is activated to absorbs food and other odors in the air being circulated through the refrigeration system of the refrigerator;

the provision of such a coated heating element to completely and efficiently remove odors from the circulating air regardless of their source so that all the food stored in the refrigerator is not effected by the odors emitted by any one food or combination of foods;

the provision of such a coating heating element in which the heating element comprises a metal rod and the coating material is a zeolite or equivalent odor absorbing material;

the provision of such a coated heating element which is a low cost heating element that is available in different sizes for use in different size refrigerators;

the provision of such a coated heating element to be readily installed and easily replaceable;

the provision of such a coated heating element in which only a portion of the rod exposed to the flow of air circulating through refrigerator is coated with the odor absorbing material; and, the provision of such a coated heating element to improve the taste of foods stored in the refrigerator even over a long period of time.

In accordance with the invention, generally stated, a deodorizing element is for use in a refrigerator. The element acts to remove food odors from the air circulating through the refrigerator which has a refrigeration system by which air is circulated throughout a food storage compartment or compartments. The deodorizing element comprises a metal rod at each end of which are electrical connectors for connecting the heating element into an electrical circuit by which current is drawn through the rod. A layer of a coating material is formed on the outer surface of the rod. This coating material is an odor absorbing material which is activated when current flows through the heating rod. The heating rod is mounted in an air circulation path of the refrigeration system by which air flowing through the system is drawn over the heating element and odors in the air are absorbed by the coating material. Other objects and features will be in part apparent and in part pointed out hereinafter.

BRIEF DESCRIPTION OF THE SEVERAL VIEWS OF THE DRAWINGS

In the drawings.

Corresponding reference characters indicate corresponding parts throughout the drawings.

DETAILED DESCRIPTION OF THE INVENTION

Figure 1:
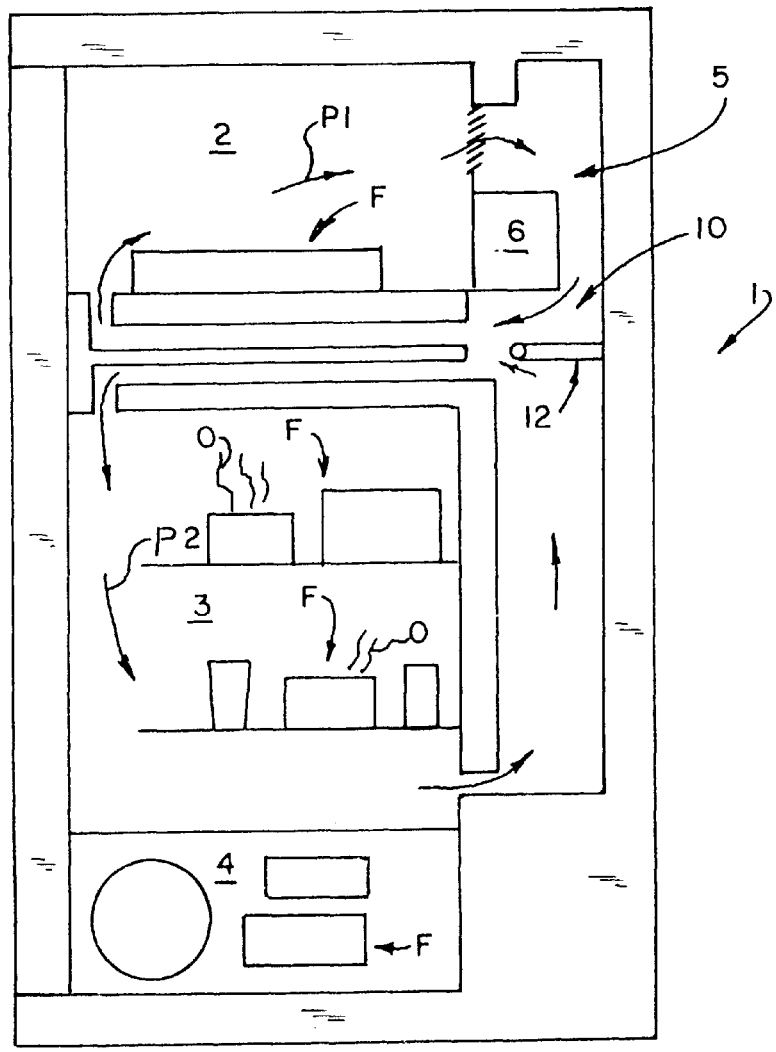
FIG. 1 is a sectional view of a refrigerator illustrating the refrigeration system of the refrigerator and installation of the deodorizing heating element of the present invention.
Figure 3:
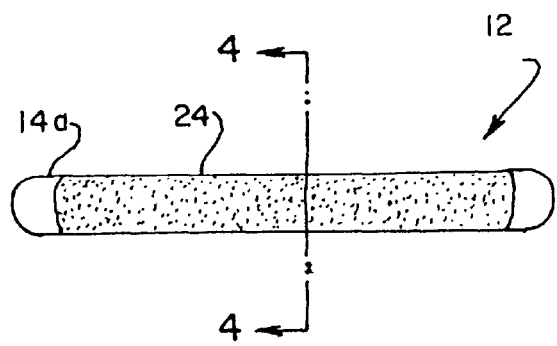
FIG. 3 is a front elevational view thereof illustrating the extent to which the heating element is coated with an odor absorbing material; and, FIG. 4 is a sectional view of the heating element taken along line 4—4 in FIG. 3.

Referring to the drawings, a refrigerator 1 is used to store food. In FIG. 1, various types of food, all of which may be packaged differently is indicated generally F. As is well-known, the refrigerator has a variety of compartments for storing food. In FIG. 1, these compartments compartment include a freezer compartment 2, general storage compartment 3, and fresh food storage compartment 4. To keep the food frozen, or at a low temperature, the refrigerator includes a refrigeration system 5. As indicated by the arrows, cold air is circulated through the respective compartment by system 5 which includes a fan (not shown) for circulating the air through a path P1 by which air is drawn through the freezer compartment or a path P2 by which it is drawn through the general storage area of the freezer, and an evaporator 6 whose operation is well-known in the art.

It is not uncommon that certain foods stored in a refrigerator give off odors O which, if absorbed by other foods can effect their taste. Various approaches have been previously tried to eliminate these odors, as indicated by the patents previously cited. An improvement of the present invention is a deodorizing means 10 by which odors emanating from various foods and permeating the circulating air are removed so that when food is removed from the refrigerator, the smell it has is uniquely its own.

Figure 4:
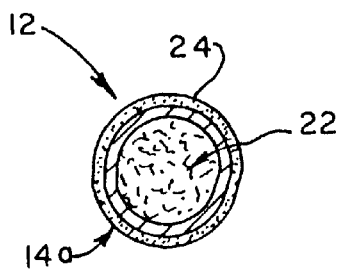
Figure 2:
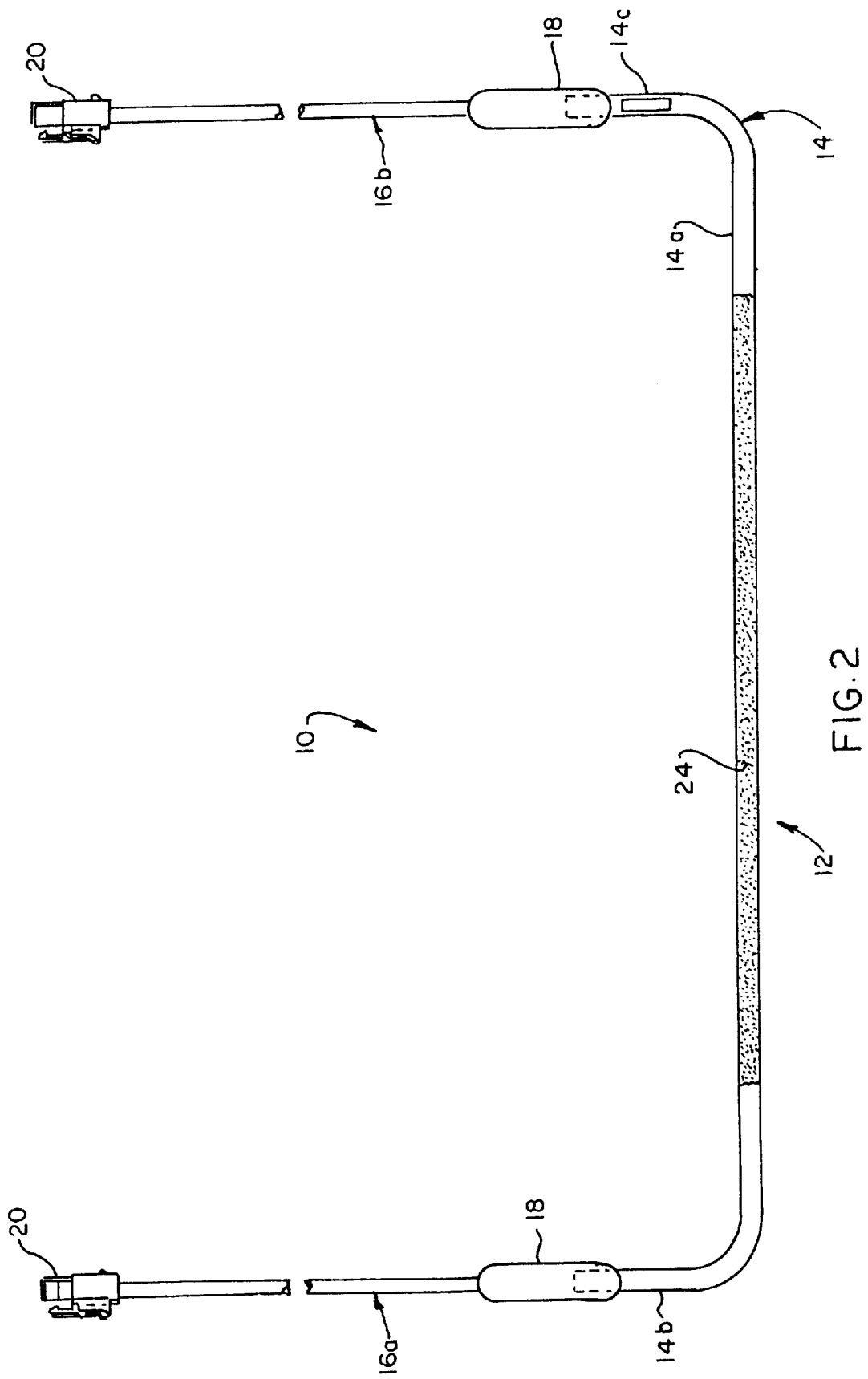
FIG. 2 is a top plan view of the deodorizing heating element.

Deodorizing means 10 includes an electrical heating element 12. As shown in FIG. 1, the heating element is located in the refrigeration system, and is installed so that air circulation over either flow path P1 or P2 flows over the heating element. Or, although not shown, a separate deodorizing means may be installed so as to be in each air flow path of the refrigeration system. The heating element is formed of a metal rod 14; which, as shown in FIG. 2, is a generally U-shaped rod having an outer diameter of 0.26" (66 mm.). The rod has a central base portion 14*a* the length of which is such that it extends substantially across the flow path or paths for the circulating air. The rod further has legs 14*b*, 14*c* at the outer ends of which are connected to electrical connection means 16*a*, 16*b* respectively. These connection means terminals each have a connector 18 into which a respective end of the rod are captured, and (female) terminals 20 for connecting the heating element into a circuit (not shown) by which electric current flows through the rod. The connection means also has an elongate central section 22 extending between each connector 18 and terminal 20. As shown in FIG. 4, the heating rod comprises a hollow tube which, during manufacture of the heating element is filled with a heat sensitive material 22 such as magnesium oxide (MgO). The magnesium oxide is compacted in the tube as part of the manufacturing process.

Next, the heating rod is coated with an odor absorbing material such as a zeolite material. This odor absorbing material is activated by the heat generated due to current flow through heating rod 14. Rod 14 is coated with a layer 24 of the zeolite or other odor absorbing material, the rod being coated to a uniform thickness. Since the heating rod is mounted in an air circulation path of the refrigeration system, air flowing through the system is drawn over the odor absorbing coating 24 on the heating element. Odors in the air are then absorbed by the coating material removing the odors from the circulating air and preventing them from contaminating other foods stored in the refrigerator. As shown in FIG. 2, only the base portion 14*a* of the heating element is coated, and then, not even the entire base portion. Heating element 10 comes in a variety of sizes so the deodorizing unit can be used in a variety of different size refrigerators. For example, for one size refrigerator, the width of the heating rod is approximately 18.3" (465 mm.) with the length of coating being approximately 16.0" (408 mm.). For another refrigerator, the length of the heating rod is approximately 25.1" (637 mm.), with the length of the coating being approximately 22.8" (580 mm.).

What has been described is a coated heating element used in a refrigerator in which food is stored. When an electrical current is supplied to the element, the coating is activated and absorbs food and other odors in the air circulating through the refrigerator's refrigeration system. The coating material acts to completely and efficiently remove odors from the circulating air regardless of their source. Thus, food stored in the refrigerator is not effected by the odors emitted by one food or combination of foods. The heating element is formed from a metal rod and the coating material is a zeolite or similar odor absorbing material. The coated heating element is a low cost heating element, available in different sizes for use in different size refrigerators, and readily installed and replaced. Use of the coated heating element in a refrigerator improves the taste of foods stored in the refrigerator even for prolonged periods of storage time.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

I claim:

1. A deodorizer for use in a refrigerator to remove food odors from the air circulating through the refrigerator, the refrigerator including refrigeration system by which air is circulated throughout a compartment in the refrigerator in which food is stored, the deodorizer comprising:

a heating element, said heating element comprising a metal rod at each end of which electrical terminals are located for connection of the heating element into a circuit by which electric current is drawn through said rod, said heating rod comprises a hollow tube filled with a compacted, current sensitive filler material; and, a coating material formed in a layer over the outer surface of the rod, said coating material being an odor absorbing material which is activated by the heat generated when current flows through the heating rod, and said heating rod being mounted in an air circulation path of the refrigeration system by which air flowing through the system is drawn over the heating element and odors in the air are absorbed by the coating material.

2. The deodorizer of claim 1 wherein said heating rod is a U-shaped rod in which the layer of coating material is formed only over the base portion of the heating element.

3. The deodorizer of claim 2 wherein said coating material is a zeolite material.

4. The deodorizer of claim 3 wherein said layer of coating material is applied over the heating rod to a uniform thickness.

5. The deodorizer of claim 4 wherein the heating rod has a diameter of approximately 0.26" (66 mm.).

6. The deodorizer of claim 1 wherein said electrical terminations are snap-fit type terminations for ease of installation and removal of the deodorizer.

7. In a refrigerator for storing food, the refrigerator having a compartment in which foods are stored and a refrigeration system by which air is circulated through the compartment to keep the foods cold, food odors emanating from some foods permeating the air and being transported thereby to other of the stored foods thereby affecting their taste, the improvement comprising deodorizing means for removing the odors from the circulating air, said deodorizing means including an electrical heating element formed of a metal rod at each end of which are located electrical terminals for connecting the heating element into a circuit by which electric current flows through said rod, and an odor absorbing material with which said heating rod is coated, said absorbing material being activated by the heat generated due to current flow through the heating rod, said heating rod being mounted in an air circulation path of the refrigeration system by which air flowing through the system is drawn over the odor absorbing coating on the heating element for odors in the air to be absorbed by the coating material, said heating rod being a hollow, U-shaped tube filled with a compacted, current sensitive filler material, said heating rod being coated only over a base portion of the heating element.

8. The improvement of claim 7 wherein said odor absorbing material is a zeolite material and coating of material is applied over the heating rod to a uniform thickness.

9. The improvement of claim 7 wherein the heating rod has a diameter of approximately 0.26" (66 mm.).

10. The improvement of claim 7 wherein said electrical terminals are snap-fit type terminations for ease of installation and removal of the rod.

11. A deodorizing heating element for removing food odors from the circulating air in a refrigerator having refrigeration system which circulates air throughout food storage compartments, the heating element comprising:

a U-shaped, hollow tubular metal rod filled with a compacted, heat sensitive material, electrical connection means at each end of the rod for connecting the heating element into an electrical circuit for conducting current through the rod; and, a coating material formed in a layer over the outer surface of a base portion of the rod, the coating material being an odor absorbing material activated by the heat generated when current flows through the heating rod, said heating rod being mounted in an air circulation path of the refrigeration system for air flowing through the system to flow over the odor absorbing coating material which absorbs the odors.

12. The heating element of claim 11 wherein said odor absorbing material is a zeolite material and a coating of the material applied to the rod being of a uniform thickness.

13. The heating element of claim 12 wherein the heating rod has a diameter of approximately 0.26" (66 mm.).

14. The heating element of claim 11 wherein said electrical connection means are snap-fit type terminations for ease of installation and removal of the heating element.

* * * * *